United States Patent [19]

Baxter

[11] 4,160,702
[45] Jul. 10, 1979

[54] ELECTROCHEMICAL MEASUREMENT OF FATIGUE DAMAGE

[75] Inventor: William J. Baxter, Bloomfield Hills, Mich.

[73] Assignee: General Motors Corporation, Detroit, Mich.

[21] Appl. No.: 898,614

[22] Filed: Apr. 21, 1978

[51] Int. Cl.² .................. G01N 27/42; G01N 3/08
[52] U.S. Cl. .................... 204/1 T; 204/58; 204/195 R
[58] Field of Search ............... 204/1 T, 195 R, 58

[56] References Cited

U.S. PATENT DOCUMENTS

| 3,408,270 | 10/1968 | Gentile | 204/1 T |
| 3,419,479 | 12/1968 | Klein | 204/1 T |
| 3,437,568 | 4/1969 | Hasselmann et al. | 204/1 T X |
| 3,710,616 | 1/1973 | Smith et al. | 204/1 T X |
| 4,019,129 | 4/1977 | Grau | 204/1 T X |

Primary Examiner—Arthur C. Prescott
Attorney, Agent, or Firm—Lawrence B. Plant

[57] ABSTRACT

Testing method for the early detection and assessment of metal fatigue damage prior to the initiation of fatigue cracks. Test parts are anodized to form an oxide coating thereon. The anodized parts are fatigue tested. Microcracks created in the oxide coating occur at the situs of deformations induced at the surface of the parts during testing. The location and extent of the microcracking is determined electrochemically by reanodizing the parts such as to anodically heal the microcracks and measuring the reanodization charge required for healing. Reanodizing incremental portions of the part point up areas of the part which allow higher current transients which in turn indicate the locations where fatigue damage is accumulating.

2 Claims, 3 Drawing Figures

ELECTROCHEMICAL MEASUREMENT OF FATIGUE DAMAGE

BACKGROUND OF THE INVENTION

This invention relates to metal fatigue testing and more particularly to testing which identifies the extent and location of fatigue damage accumulation prior to the initiation of fatigue cracks.

The early detection and assessment of the accumulation of fatigue damage in metal parts is an old and complex problem. A wide variety of methods have been explored but with very limited success. The objective has heretofore usually been to detect the initial fatigue crack. Such observations provide useful information but do not provide a means to estimate the severity of the damage in terms of the remaining portion of the useful fatigue life. I have earlier observed and reported (e.g., Metallurgical Transactions A, Vol. 8A, 899–904, June 1977) that an early manifestation of the accumulation of fatigue damage is the development of surface deformation at certain locations of the part during fatigue testing which locations eventually become sites for nucleation of fatigue cracks. I have further observed that long before fatigue cracks appear in the metal, the surface deformation produced microcracks in the natural layer of brittle surface oxide that forms on the metal and that the bare metal at the base of the microcracks could be located and quantified by scanning the specimen's surface with a small spot of ultraviolet radiation and measuring the region where intense exoelectron emission developed. While this process was effective, the procedure was complex, time consuming and required rather expensive and sophisticated equipment.

It is an object of the present invention to provide a simpler method for the early detection and assessment of the accumulation of fatigue damage in metal parts prior to the initiation of fatigue cracks in the parts and without the need for complex procedures and equipment. This and other objects and advantages of the present invention will become more apparent from the detailed description thereof which follows.

THE INVENTION

The invention contemplates: anodizing the surface of a metal part at an arbitrarily selected predetermined voltage to build up a current-limiting oxide coating on the part which cuases the anodizing current to decline with time to an arbitrarily selected cut-off level; fatigue testing the part according to a prescribed regimen sufficient to cause localized deformation of the part's surface and microcracking of the oxide layer at the situs of the deformations; reanodizing the part at the anodizing voltage or less and allowing the reanodizing current to decline to about said predetermined cut-off current to oxidatively heal said microcracks; and measuring the localized and total current transients on said part as a measure of the location and extent of the microcracking. In this regard, the total reanodization transient charge (i.e., coulombs) required to heal or reanodize the microcracks indicates the total damage or surface deformation induced by the fatigue testing and the location of the highest current transient on the part indicate the location on the parts where the damage has occurred.

In order to evaluate the results obtained during reanodization, it is necessary to know how (i.e., voltage-current) the original oxide coating was formed. In this regard, during the anodizing process there is an initially high flow of current when the bare metal is directly in contact with the electrolyte, but the anodizing current rapidly declines to a significantly lower level as the highly resistive oxide coating builds up and passivates the metal part. The precise nature of the oxide coating will depend on the metal being anodized, the electrolyte employed, the anodizing potential (i.e., voltage) and the cut-off current selected. The particular combination of anodizing conditions is not particularly important—rather only that they be known and substantially reproducible during the reanodization step.

Figure 2:
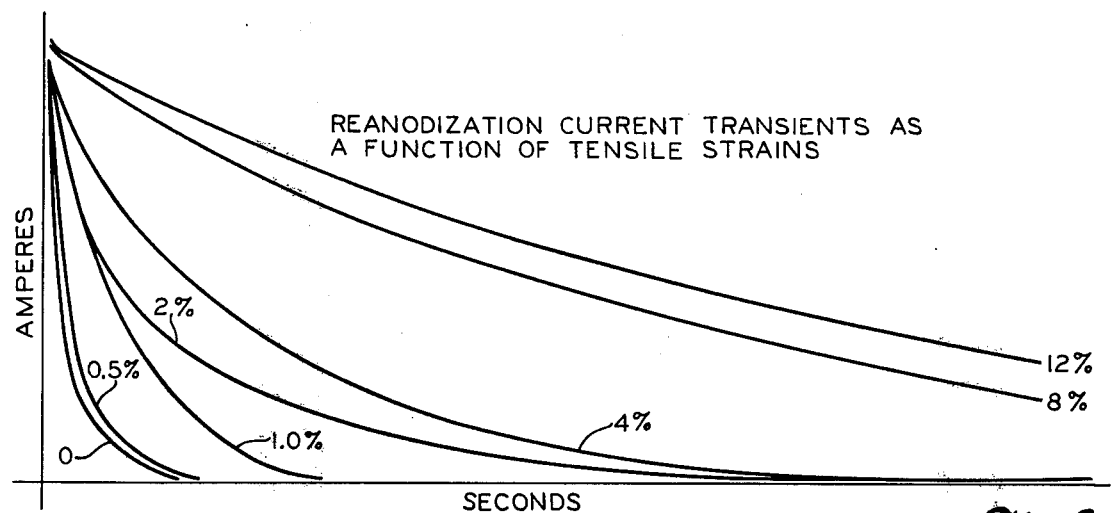
FIG. 2 is a draftsman's illustration of typical current flows observed in testing the present invention.

Following fatigue testing (e.g., bending, twisting, etc.) as required for the particular part, the part is reanodized under substantially the same conditions as the initial anodization. In this regard, the reanodization voltage should be no more than the anodization voltage or else the overall coating thickness would increase and tend to mask the significance of the current transients as they relate to the microcracks. Preferably, the reanodization voltage is slightly less than the anodization voltage to insure that all the current transients result from microcrack healing. During reanodization the current drops to substantially the same cut-off current as was used in the anodization so that only that charge that goes into healing the microcracks is determined. The total transient charge (i.e., coulombs) passed during reanodization indicates the extent of microcrack healing which is directly related to the extent the surface was deformed during the fatigue testing. In this regard, FIG. 2 illustrates typical current transients for parts strained to various levels and shows that as the strain increases the microcracks take longer to heal and the transient charge (i.e., area under each curve) increases significantly. The current decay illustrated in FIG. 2, in fact, consists of two decay stages—the first being due to the initial charging of the oxide film and the second due to the reanodization of the cracks.

Figure 1:
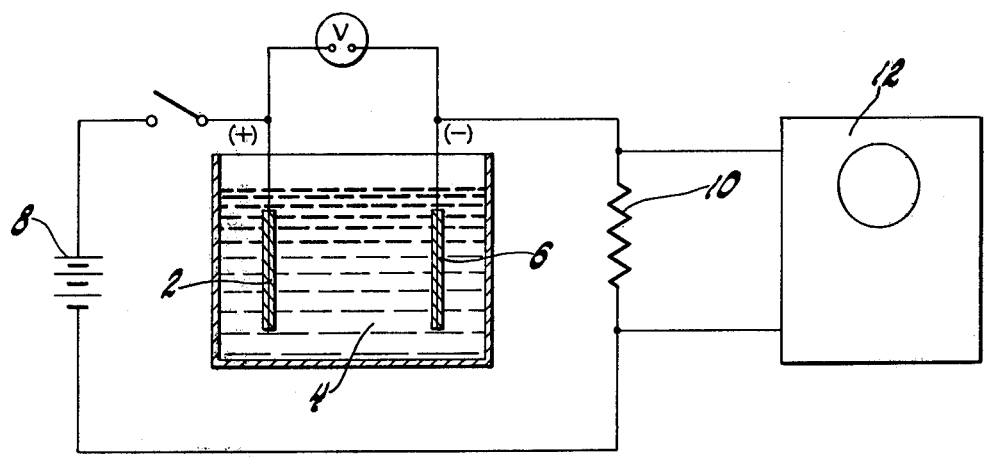
FIG. 1 depicts the test apparatus for determining the electrochemical current transients of the present invention.

Initial anodization and reanodization is performed in apparatus such as shown in FIG. 1 in order that the anodization and reanodization conditions can be accurately determined and duplicated. The test specimen 2 is immersed and anodically polarized in an electrolyte 4 appropriate to the composition of the specimen 2. A cathodically polarized counterelectrode 6 is positioned opposite the specimen 2 in the electrolyte 4. Appropriate means (e.g., battery, rectifier, etc.) 8 are provided to impress anodizing and reanodizing potential/current on the electrodes. A resistor 10 is connected in series with the means 8 and electrodes 2–6 and a recording, digital storage oscilloscope 12 is used to record the current transients such as illustrated in FIG. 2.

In accordance with a further aspect of the invention, reanodizing incremental portions of the part permits mapping of the part in the sense of locating the regions on the part where microcracking of the oxide has occurred. One way of accomplishing this is to slowly immerse the part 2 into the electrolyte 4 during reanodization and observing the current transient at each stage of the immersion. As areas of the part containing oxide microcracks become submerged in the electrolyte, the current flow increases in direct relation to the extent of the microcracks contacting the electrolyte. By plotting the current flow against the depth of immersion, the location of the microcracked regions, at least along one axis of the part, can be determined. To more specifically locate the strained regions the same part is fatigued again in the same manner as before to induce more oxide microcracks at substantially the same locations where they had been first formed and later healed in the first slow immersion. The thusly recracked part is then again slowly immersed into the electrolyte, but this time in another orientation (e.g., 90° from the axis of the first slow immersion) and again the current is plotted against the depth of immersion. By overlaying the current's immersion depth plots for the two slow immersions a coordinate grid system (i.e., x-y diagram) is provided from which the profile of the fatigue damage and its location on the part is readily seen.

Another way of reanodizing incremental portions of the part to map the fatigue damaged areas is to anodically scan the part with a cathodic probe having an electrolyte-wetted tip (e.g., electrolyte soaked felt tip). As with the slow immersion technique, the current flowing to the part through the tip of the probe is recorded at each increment of the surface as the cathode progressively traverses/scans the surface of the part.

Figure 3:
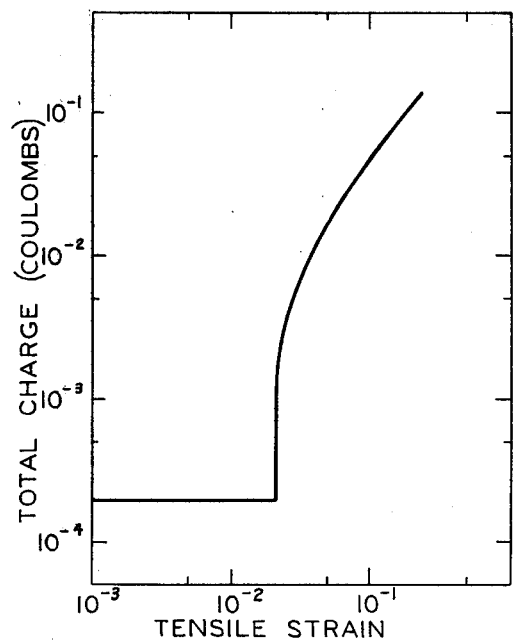
FIG. 3 is a plot of the total charge versus the tensile strain of one specific example of the invention.

FIG. 3 is a plot of the results obtained in one specific feasibility test of the invention and is a plot of the total charge flowing to previously anodized 1100-0 aluminum specimens during reanodization thereof following tensile straining in an Instron machine. The several specimens were strained to different levels by known amounts as determined by the movement of the Instron's crosshead which had been earlier calibrated with an extensometer using identical specimens.

Prior to tensile testing the specimens were anodized in a 3% by weight tartaric acid electrolyte (i.e., acid adjusted to a pH of 5 with ammonium hydroxide) using another piece of aluminum as the cathode. At the beginning of the anodization and before any significant oxide had formed, the applied voltage was gradually increased to the desired voltage so as to keep the anodization current density below about 10 milliamperes per square centimeter ($ma/cm^2$). When the desired anodization voltage (i.e., here about 20 volts) was achieved, the voltage was held constant but the current allowed to decline from the initial 10 $ma/cm^2$ rate to an arbitrarily selected cut-off level of about $1 \times 10^{-3}$ $ma/cm^2$ at the end of about twenty minutes during which time an oxide coating of about twenty-eight nanometers was produced on the surface of the specimen.

The specimens were then tensile strained as discussed above and then reanodized in accordance with the present invention. The Instron machine severely deformed the ends of the specimens so it was first necessary to reanodize the ends of the specimens exactly as before and before reanodizing the gage sections of the specimens. The gage sections of the samples were then reanodized but at a slightly lower voltage than the initial anodization voltage, and the current transient recorded. From the current transient, the total charge flowing to each specimen is computed and related to the amount of strain experienced by the specimen (i.e., see FIG. 3). The horizontal portion of the curve of FIG. 3 indicates that microcracks in the oxide do not begin to form until after the specimen has experienced a strain of about $2 \times 10^{-2}$ and the charge transient up to that point is solely that required to charge the still intact oxide film. Above a strain of about $2 \times 10^{-2}$ microcracks form revealing fresh metal for reanodization and the charge transient climbs rapidly in direct relation to the amount of strain experienced by the specimen.

While this invention has been exemplified primarily in terms of aluminum, it is likewise applicable to other metals susceptible to controllable anodic oxidation as is well known in the art (e.g., L. Young, *Anodic Oxide Films,* Academic Press, 1961). Hence, this invention is not intended to be limited to the extent set forth hereafter in the claims which follow.

The embodiments of the invention in which an exclusive property or privilege is claimed are defined as follows:

1. A testing method for the early detection and assessment of the accumulation of fatigue damage in metal parts prior to the formation of detectable fatigue cracks therein comprising the steps of:

anodizing the surface of said part in an appropriate electrolyte to form a current-limiting oxide coating thereon said anodizing proceeding to a predetermined cut-off current at a predetermined anodizing potential;

fatigue testing the parts according to a prescribed regimen for a sufficient amount to induce the formation of microcracks in said coating at the situs of deformations induced on said surface by said testing which deformations are precursors of said fatigue cracks;

anodizing said part in said electrolyte at a potential of about said predetermined anodizing potential or less until the reanodization current falls off to about said predetermined cut-off current to anodically heal said microcracks; and determining the transient charge required to heal said microcracks as an indicator of the extent of fatigue accumulated in the part by said fatigue testing.

2. A testing method for the early detection and assessment of the accumulation of fatigue damage in metal parts prior to the formation of detectable fatigue cracks therein comprising the steps of:

anodizing the surface of said part in an appropriate electrolyte to form a current-limiting oxide coating thereon;

fatigue testing the parts according to a prescribed regimen for sufficient amount to induce the formation of microcracks in said coating at the situs of deformations induced on said surface by said testing which deformations are the precursors of said fatigue cracks;

anodically scanning said part by progressively reanodizing said part and noting the reanodization current transient at each stage of the progression to identify regions of the part where high current transients occur which are indicative of the situs of said microcracks and hence the potential situs of said fatigue cracks.

* * * * *